United States Patent
Yang et al.

(10) Patent No.: US 11,547,488 B2
(45) Date of Patent: Jan. 10, 2023

(54) SYSTEMS AND METHODS FOR PERFORMING INTRAOPERATIVE IMAGE REGISTRATION

(71) Applicant: 7D SURGICAL INC., Toronto (CA)

(72) Inventors: Victor X. D. Yang, North York (CA); Adrian Mariampillai, Toronto (CA); Michael Leung, Markham (CA); Peter Siegler, Toronto (CA); Beau Anthony Standish, Toronto (CA)

(73) Assignee: 7D SURGICAL ULC, Toronto (CA)

( * ) Notice: Subject to any disclaimer, the term of this patent is extended or adjusted under 35 U.S.C. 154(b) by 1045 days.

(21) Appl. No.: 16/314,826

(22) PCT Filed: Jul. 4, 2017

(86) PCT No.: PCT/CA2017/050807
§ 371 (c)(1),
(2) Date: Jan. 2, 2019

(87) PCT Pub. No.: WO2018/006168
PCT Pub. Date: Jan. 11, 2018

(65) Prior Publication Data
US 2019/0350658 A1     Nov. 21, 2019

Related U.S. Application Data

(60) Provisional application No. 62/358,250, filed on Jul. 5, 2016.

(51) Int. Cl.
*A61B 5/05* (2021.01)
*A61B 34/20* (2016.01)
(Continued)

(52) U.S. Cl.
CPC ............ *A61B 34/20* (2016.02); *A61B 5/0035* (2013.01); *A61B 5/055* (2013.01); *A61B 6/032* (2013.01);
(Continued)

(58) Field of Classification Search
CPC combination set(s) only.
See application file for complete search history.

(56) References Cited

U.S. PATENT DOCUMENTS 9,119,670 B2    9/2015  Yang et al.
2006/0030768 A1*  2/2006  Ramamurthy ........ G06T 7/0012
                                                       600/407

(Continued)

FOREIGN PATENT DOCUMENTS

WO    2008103383 A1    8/2008
WO    2011134083 A1    11/2011
WO    2015074158 A1    5/2015

OTHER PUBLICATIONS

International Search Report for the parent PCT application PCT/CA2017/050807, dated Nov. 14, 2017.
(Continued)

*Primary Examiner* — Joel F Brutus
(74) *Attorney, Agent, or Firm* — Hill & Schumacher

(57) ABSTRACT

Systems and methods are provided for performing intraoperative fusion of two or more volumetric image datasets via surface-based image registration. The volumetric image datasets are separately registered with intraoperatively acquired surface data, thereby fusing the two volumetric image datasets into a common frame of reference while avoiding the need for complex and time-consuming preoperative volumetric-to-volumetric image registration and
(Continued)

fusion. The resulting fused image data may be processed to generate one or more images for use during surgical navigation.

34 Claims, 10 Drawing Sheets

(51) Int. Cl.
*A61B 90/00* (2016.01)
*G06T 7/521* (2017.01)
*G06T 7/37* (2017.01)
*A61B 5/00* (2006.01)
*A61B 5/055* (2006.01)
*A61B 6/03* (2006.01)
*A61B 6/12* (2006.01)
*A61B 6/00* (2006.01)

(52) U.S. Cl.
CPC .............. *A61B 6/12* (2013.01); *A61B 6/5247* (2013.01); *A61B 90/39* (2016.02); *G06T 7/37* (2017.01); *G06T 7/521* (2017.01); *A61B 2034/2051* (2016.02); *A61B 2034/2055* (2016.02); *A61B 2034/2065* (2016.02); *A61B 2090/3937* (2016.02); *G06T 2207/10081* (2013.01); *G06T 2207/10088* (2013.01); *G06T 2207/20221* (2013.01); *G06T 2207/30004* (2013.01); *G06T 2207/30204* (2013.01)

(56) References Cited

U.S. PATENT DOCUMENTS

| | | |
|---|---|---|
| 2008/0063301 A1 | 3/2008 | Bogoni et al. |
| 2008/0269588 A1 | 10/2008 | Csavoy et al. |
| 2010/0054525 A1 | 3/2010 | Gong et al. |
| 2015/0371361 A1* | 12/2015 | Kim .......................... G06T 7/33 382/128 |
| 2016/0191887 A1* | 6/2016 | Casas ...................... G06F 3/017 348/47 |

OTHER PUBLICATIONS

Herring, Jeannette and Benoit Dawant, "Automatic Lumbar Vertebral Identification Using Surface-Based Registration", Journal of Biomedical Informatics 34, 74-87, (2001).

* cited by examiner

SYSTEMS AND METHODS FOR PERFORMING INTRAOPERATIVE IMAGE REGISTRATION

CROSS-REFERENCE TO RELATED APPLICATION

This application is a National Phase application claiming the benefit of the international PCT Patent Application No. PCT/CA2017/050807, filed on Jul. 4, 2017, in English, which claims priority to U.S. Provisional Application No. 62/358,250, titled "SYSTEMS AND METHODS FOR PERFORMING INTRAOPERATIVE IMAGE REGISTRATION" and filed on Jul. 5, 2016, the entire contents of which are incorporated herein by reference.

BACKGROUND

This disclosure relates generally to surgical systems and methods, and more particularly to systems and methods for performing surgical navigation.

Image fusion is a technique used to represent or overlay multiple images, often obtained using different imaging modalities, into a single coordinate system in order to support the visualization of different aspects of the patient's anatomy/pathology. For example, the fusion of magnetic resonance imaging (MRI) image data and computed tomography (CT) image data enables a user or operator to view image data of soft tissue from the MRI scan overlaid onto bone and/or vasculature image data from the CT scan.

SUMMARY

Systems and methods are provided for performing intraoperative fusion of two or more volumetric image datasets via surface-based intraoperative image registration. The volumetric image datasets are separately registered with intraoperatively acquired surface data, thereby fusing the two volumetric image datasets into a common frame of reference while avoiding the need for time-consuming and inaccurate preoperative volumetric-to-volumetric image registration and fusion. The resulting fused image data may be processed to generate one or more images for use during surgical navigation.

Accordingly, in a first aspect, there is provided a method of performing intraoperative image registration, the method comprising:

obtaining a first volumetric image dataset pertaining to a subject;

obtaining a second volumetric image dataset pertaining to the subject; processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

receiving input identifying at least three first fiducial points associated with the first surface dataset;

receiving input identifying at least three second fiducial points associated with the second surface dataset, wherein each second fiducial point corresponds to a respective first fiducial point;

intraoperatively detecting, with a surface detection subsystem, intraoperative surface data characterizing an intraoperatively exposed surface region, wherein the intraoperatively exposed surface region overlaps with at least a portion of the first anatomical surface region and at least a portion of the second anatomical surface region;

obtaining input identifying at least three intraoperative fiducial points in an intraoperative frame of reference associated with the intraoperative surface data, wherein each intraoperative fiducial point corresponds to a respective first fiducial point;

employing the first fiducial points and the corresponding intraoperative fiducial points to perform registration between the first anatomical surface dataset and the intraoperative surface data, thereby obtaining a first registration transform;

employing the second fiducial points and the corresponding intraoperative fiducial points to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

receiving input identifying at least three first fiducial points associated with the first surface dataset;

receiving input identifying at least three second fiducial points associated with the second surface dataset, wherein each second fiducial point corresponds to a respective first fiducial point;

controlling said surface detection subsystem to intraoperatively detect intraoperative surface data characterizing an intraoperatively exposed surface region, wherein the intraoperatively exposed surface region overlaps with at least a portion of the first anatomical surface region and at least a portion of the second anatomical surface region;

obtaining input identifying at least three intraoperative fiducial points in an intraoperative frame of reference associated with the intraoperative surface data, wherein each intraoperative fiducial point corresponds to a respective first fiducial point;

employing the first fiducial points and the corresponding intraoperative fiducial points to perform registration between the first anatomical surface dataset and the intraoperative surface data, thereby obtaining a first registration transform;

employing the second fiducial points and the corresponding intraoperative fiducial points to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a method of performing intraoperative image registration, the method comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

receiving input identifying at least three first fiducial points associated with the first surface dataset;

receiving input identifying at least three second fiducial points associated with the second surface dataset, wherein each second fiducial point corresponds to a respective first fiducial point;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

intraoperatively detecting, with the surface detection subsystem, second intraoperative surface data characterizing a second intraoperatively exposed surface region, wherein the second intraoperatively exposed surface region overlaps with at least a portion of the second anatomical surface region;

obtaining input identifying at least three primary intraoperative fiducial points in an intraoperative frame of reference, wherein each primary intraoperative fiducial point corresponds to a respective first fiducial point;

obtaining input identifying at least three secondary intraoperative fiducial points in the intraoperative frame of reference, wherein each secondary intraoperative fiducial point corresponds to a respective second fiducial point;

employing the first fiducial points and the corresponding primary intraoperative fiducial points to perform registration between the first anatomical surface dataset and the first intraoperative surface data, thereby obtaining a first registration transform;

employing the second fiducial points and the corresponding secondary intraoperative fiducial points to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

receiving input identifying at least three first fiducial points associated with the first surface dataset;

receiving input identifying at least three second fiducial points associated with the second surface dataset, wherein each second fiducial point corresponds to a respective first fiducial point;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

controlling said surface detection subsystem to intraoperatively detect intraoperative surface data characterizing a second intraoperatively exposed surface region, wherein the second intraoperatively exposed surface region overlaps with at least a portion of the second anatomical surface region;

obtaining input identifying at least three primary intraoperative fiducial points in an intraoperative frame of reference, wherein each primary intraoperative fiducial point corresponds to a respective first fiducial point;

obtaining input identifying at least three secondary intraoperative fiducial points in the intraoperative frame of reference, wherein each secondary intraoperative fiducial point corresponds to a respective second fiducial point;

employing the first fiducial points and the corresponding primary intraoperative fiducial points to perform registration between the first anatomical surface dataset and the first intraoperative surface data, thereby obtaining a first registration transform;

employing the second fiducial points and the corresponding secondary intraoperative fiducial points to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a method of performing intraoperative image registration, the method comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, intraoperative surface data characterizing an intraoperatively exposed surface region, wherein the intraoperatively exposed surface region overlaps with at least a portion of the first anatomical surface region and at least a portion of the second anatomical surface region;

employing first fiducial points identified within the first anatomical surface dataset and corresponding intraoperative fiducial points identified in the intraoperative surface data to perform registration between the first anatomical surface dataset and the intraoperative surface data, thereby obtaining a first registration transform;

employing second fiducial points identified within the second anatomical surface dataset and corresponding intraoperative fiducial points identified in the intraoperative surface data to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

controlling said surface detection subsystem to intraoperatively detect intraoperative surface data characterizing an intraoperatively exposed surface region, wherein the intraoperatively exposed surface region overlaps with at least a portion of the first anatomical surface region and at least a portion of the second anatomical surface region;

employing first fiducial points identified within the first anatomical surface dataset and corresponding intraoperative fiducial points identified within the intraoperative surface data to perform registration between the first anatomical surface dataset and the intraoperative surface data, thereby obtaining a first registration transform;

employing second fiducial points identified within the second anatomical surface dataset and corresponding intraoperative fiducial points identified within the intraoperative surface dataset to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a method of performing intraoperative image registration, the method comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

intraoperatively detecting, with the surface detection subsystem, second intraoperative surface data characterizing a second intraoperatively exposed surface region, wherein the second intraoperatively exposed surface region overlaps with at least a portion of the second anatomical surface region;

employing first fiducial points identified within the first anatomical surface dataset and corresponding primary intraoperative fiducial points identified within the first intraoperative surface data to perform registration between the first anatomical surface dataset and the first intraoperative surface data, thereby obtaining a first registration transform;

employing second fiducial points identified within the second anatomical surface dataset and corresponding secondary intraoperative fiducial points identified within the second intraoperative surface data to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

In another aspect, there is provided a system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

controlling said surface detection subsystem to intraoperatively detect intraoperative surface data characterizing a second intraoperatively exposed surface region, wherein the second intraoperatively exposed surface region overlaps with at least a portion of the second anatomical surface region;

employing first fiducial points identified within the first anatomical surface dataset and corresponding primary intraoperative fiducial points identified within the first intraoperative surface dataset to perform registration between the first anatomical surface dataset and the first intraoperative surface data, thereby obtaining a first registration transform;

employing second fiducial points identified within the second anatomical surface dataset and corresponding secondary intraoperative fiducial points identified within the second anatomical surface dataset to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
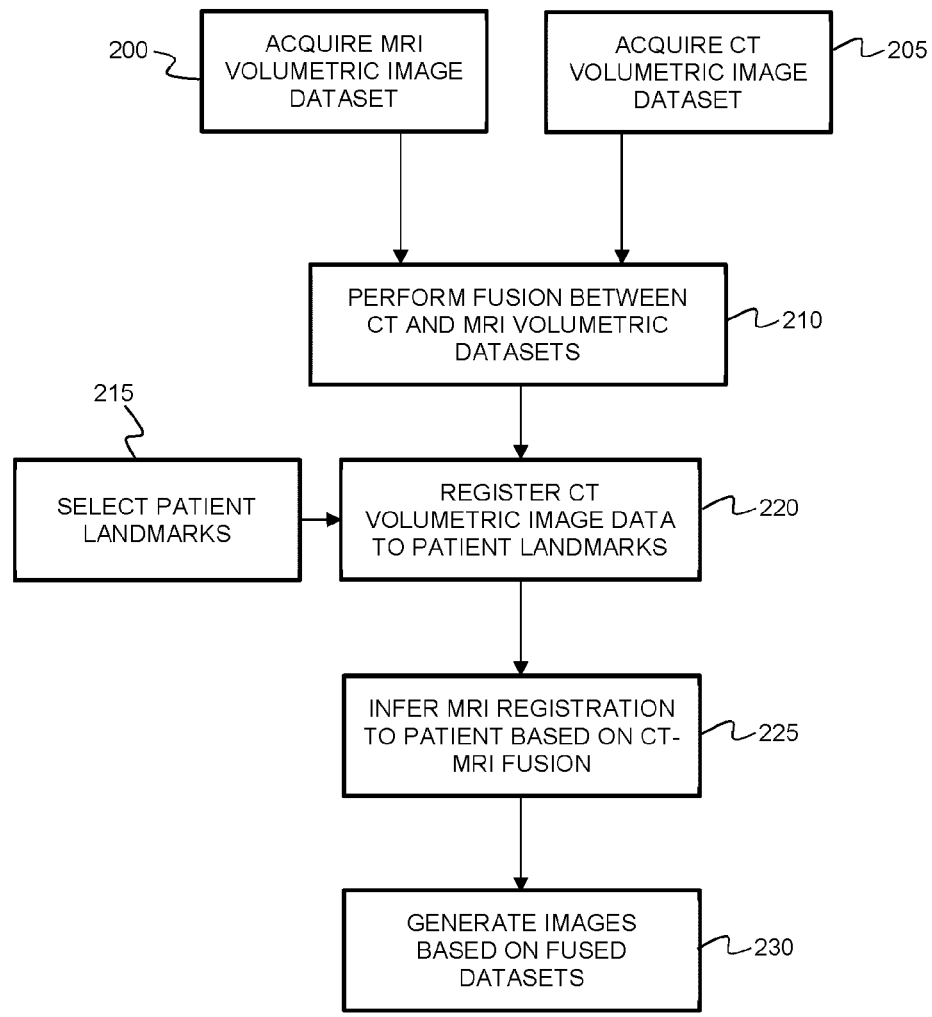
FIG. 1A is a flow chart illustrating a conventional method of performing volumetric-registration-based image fusion between MRI and CT volumetric image data.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups. As used herein, the term "on the order of", when used in conjunction with a quantity or parameter, refers to a range spanning approximately one tenth to ten times the stated quantity or parameter.

As used herein, the phrase "image fusion" refers to the transformation of image data from two or more volumetric image datasets, so that the volumetric image datasets are represented in a common frame of reference, with a common coordinate system. Fused volumetric datasets may, in some example implementations, be employed to generate and display an image that includes image data from the two or more of the fused volumetric image datasets. However, it will be understood that an image generated from fused volumetric image datasets need not include image data from two or more of the volumetric image datasets. For example, multiple images may be separately generated based on the fused volumetric image datasets, with two or more separate images separately displaying respective image data from different volumetric image datasets in the common coordinate system.

As used herein, the phrase "intraoperative" refers to an event that occurs during a surgical procedure, including events before or after a phase of a surgical procedure. For example, an intraoperative measurement involving the surface topography of an exposed potion of the cranial anatomy may occur any time that cranial tissue is exposed, such as during an interventional phase of surgical procedure, and after the interventional phase, or prior to the interventional phase of a procedure.

As described above, MR-CT fusion is a volumetric registration method in which MR and CT images are represented in a common frame of reference (having a common coordinate system). Fused datasets can be used during surgical navigation in order to enable surgical navigation via both imaging modalities. A conventional image fusion workflow is shown in FIG. 1A, in which MR and CT image datasets are merged pre-operatively via a volumetric-to-volumetric image registration method, prior to intraoperative registration. As shown at steps 200 and 205, an MRI image dataset and a CT image dataset are respectively acquired. A volumetric registration method is then employed to perform preoperative image registration between the MRI image dataset and the CT image dataset, as shown at step 210. One of the preoperative image datasets, (typically the CT image dataset, as shown at step 220) is then registered to the patient intraoperatively using fiducial markers (landmarks). The registration of the MRI volumetric image data is inferred based on the CT-MR fusion at step 225, and the fused (merged) datasets, which are now both registered to an intraoperative frame of reference, may be employed to generate intraoperative images for navigated procedures, as shown at step 230.

Unfortunately, the workflow shown in FIG. 1A has a number of associated drawbacks. Firstly, the method is time consuming, as surgeons have traditionally required additional user interaction in preoperative data fusion, organized as a separate step prior to surgical navigation registration. This fusion step, involving registration between two volumetric image datasets, involves long computational times. Due to the long navigation registration time, the data fusion, whether semi- or fully automatic, is typically viewed as a necessary step prior to the start of a surgical procedure.

Figure 1B:
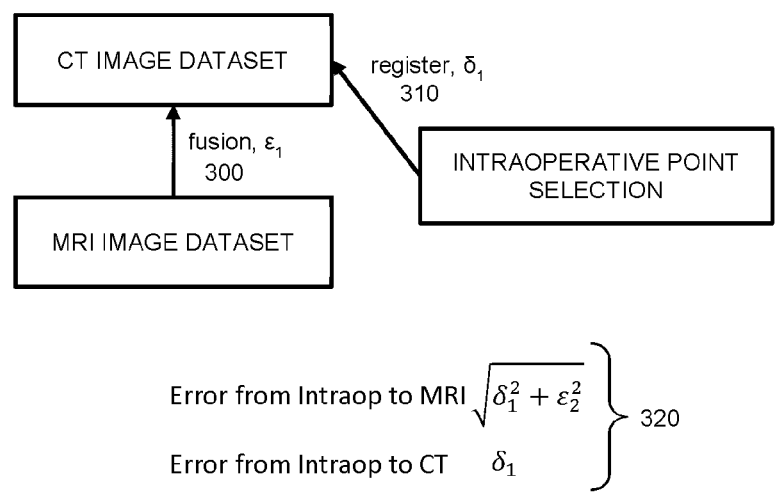
FIG. 1B illustrates the errors introduced when image fusion is performed according to the conventional volumetric registration method shown in FIG. 1A.

Another significant drawback of the conventional image fusion method illustrated in FIG. 1A is the propagation and accumulation of registration errors, which can contribute to increased errors during navigation. For example, as shown in FIG. 1B, if the MR-CT fusion step 300 introduces an error $\varepsilon_1$, and the error associated with the CT to patient registration 310 is $\delta_1$, then as shown qualitatively at 320, the net error associated with MR to patient registration based on the fusion step is:

$$\sqrt{\varepsilon_1^2 + \delta_1^2}. \quad (1)$$

Another drawback of the conventional registration process shown in FIG. 1A may require preoperative fiducial markers to be present in either the MRI of CT scan. The incorporation of such physical fiducial markers can necessitate the performing of a CT and/or MRI scan on the same day of a procedure. Furthermore, the conventional methods illustrated in FIG. 1A results in navigational accuracy that decreases due to sparse patient fiducials, worsening as a function of distance away from registration point (e.g. the back of the head is inaccurate when registering to the face).

Various example embodiments of the present disclosure aim to address the aforementioned shortcomings by providing systems and methods for performing intraoperative fusion of two or more volumetric image datasets during (or after) a medical procedure via the registration of the volumetric image datasets with intraoperative surface data. As explained in detail below, the example embodiments disclosed herein employ the use of intraoperatively acquired surface data for registration of the volumetric image datasets, where each volumetric image dataset is registered to intraoperative surface data to bring the two (or more) volumetric image datasets into a common frame of reference while avoiding the need for complex and time-consuming preoperative volumetric-to-volumetric image registration and fusion.

Figure 2:
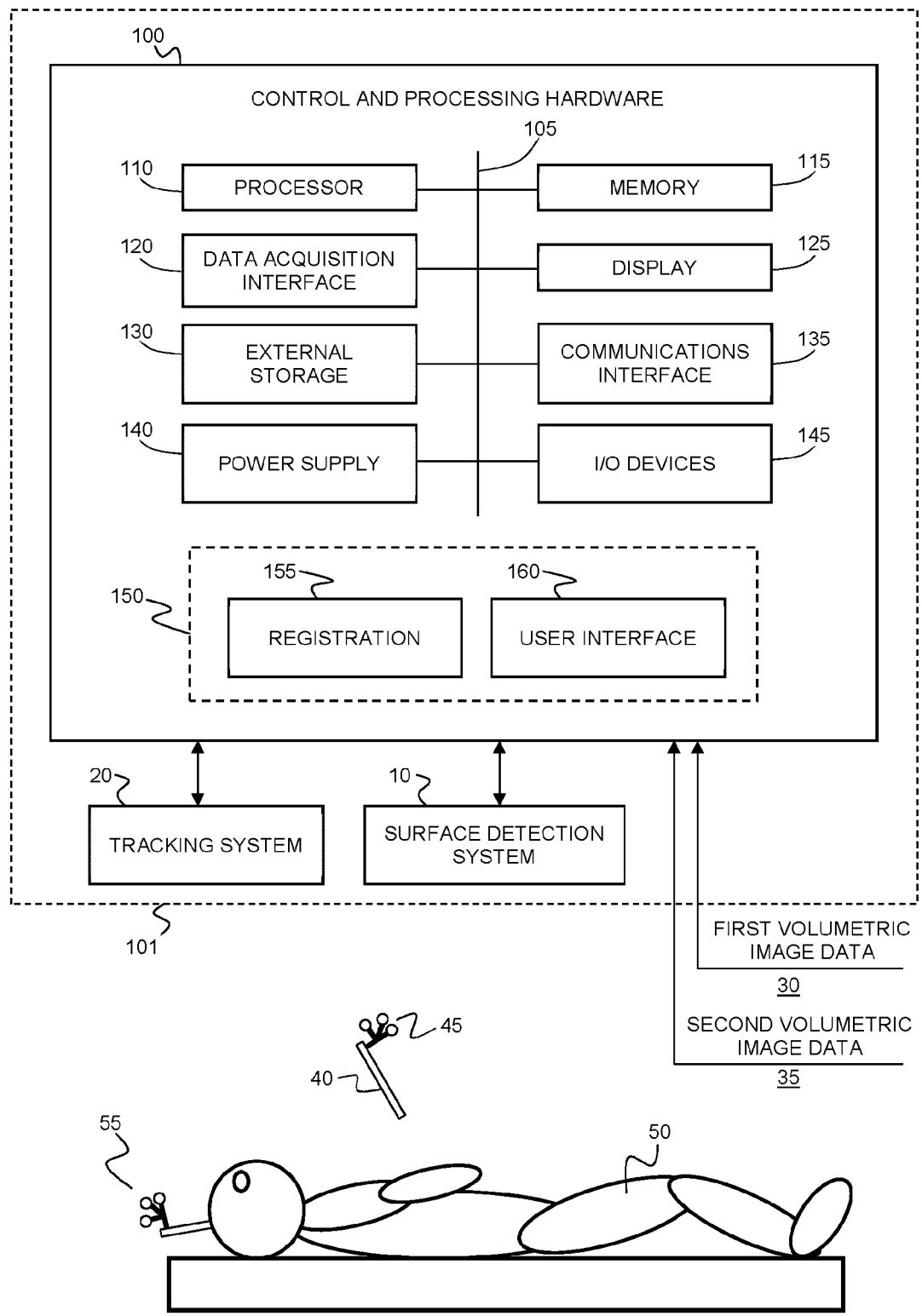
FIG. 2 shows an example system for performing intraoperative image fusion based on surface detection.

Referring now to FIG. 2, an example system is shown for performing intraoperative image fusion. The system includes a surface detection system 10 that is operably interfaced with control and processing hardware 100. The surface detection system 10 may be any suitable system for detecting, measuring, imaging, or otherwise determining the surface topography of one or more objects (such as, but not limited to, an exposed cranial tissue region of a subject 50, such the skin, the skull, or underlying tissues) using optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

The example system may also include a tracking system 20, which may be employed to track the position and orientation of one or more medical instruments 40. The medical instrument 40 is shown having fiducial markers 45 attached thereto, and passive or active signals emitted from the fiducial markers 45 are detected by the tracking system 20 (e.g. a stereoscopic tracking system employing two tracking cameras). In an alternative example embodiment, the position and orientation of a medical instrument may be tracked via a surface detection subsystem 10, such as a structured light detection system, that is employed to detect the surface profile of at least a portion of the medical instrument, or structure attached thereto, and to determine the position and orientation of the medical instrument via comparison of the detected surface profile with a known surface profile.

As also shown in FIG. 2, a tracked reference frame 55 (e.g. a clamp with fiducial markers provided thereon or attached thereto) may be attached to the patient and may be tracked by the tracking system 20. Such a tracked reference frame 55 may be employed for image guided surgeries.

FIG. 2 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 2 is illustrative of a non-limiting example embodiment, and is not intended to be limited to the components shown. Furthermore, one or more components of the control and processing hardware 100 may be provided as an external component that is interfaced to a processing device. For example, as shown in the figure, one or both of the surface detection system 10 and the tracking system 20 may be included as a component of control and processing hardware 100 (as shown within the dashed line 101), or may be provided as one or more external devices.

Although only one of each component is illustrated in FIG. 2, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, which include executable instructions, which when executed by the one or more processors 110, causes the system to perform one or more methods described in the present disclosure. Such instructions may be stored, for example, in memory 115 and/or other internal storage. In particular, in the example embodiment shown, registration module 155 includes executable instructions for registering surface data (obtained from the first volumetric image data 30 and the second volumetric image data 35) with intraoperative surface data that is obtained using the surface detection system 10, and for performing image fusion of the first volumetric image data 30 and the second volumetric image data 35 based on the detected surface. The navigation user interface module 160 includes executable instructions for displaying a user interface for performing, for example, image-guided surgical procedures and displaying fused volumetric images.

Various example embodiments of the present disclosure that involve the intraoperative fusion of at least two volumetric image datasets based on detected surface data employ the registration of surface data (obtained by processing the volumetric image data) with intraoperative surface data (intraoperatively obtained using a surface detection system; also known as a surface topography detection system or surface profile detection system), in order to achieve intraoperative image fusion of the volumetric image datasets. The example embodiments disclosed below are illustrated within the example context of cranial procedures in which surface detection is employed to detect intraoperative surface data from a portion of the cranial anatomy that is intraoperatively exposed. However, it will be understood that these examples are not intended to limit the scope of the present disclosure to cranial procedures. As described in further detail below, the example embodiments described below may be adapted to a wide variety of surgical procedures involving various different anatomical regions. The embodiments provided below that pertain to cranial procedures are but one example application of the presently disclosed systems and methods.

Figure 3A:
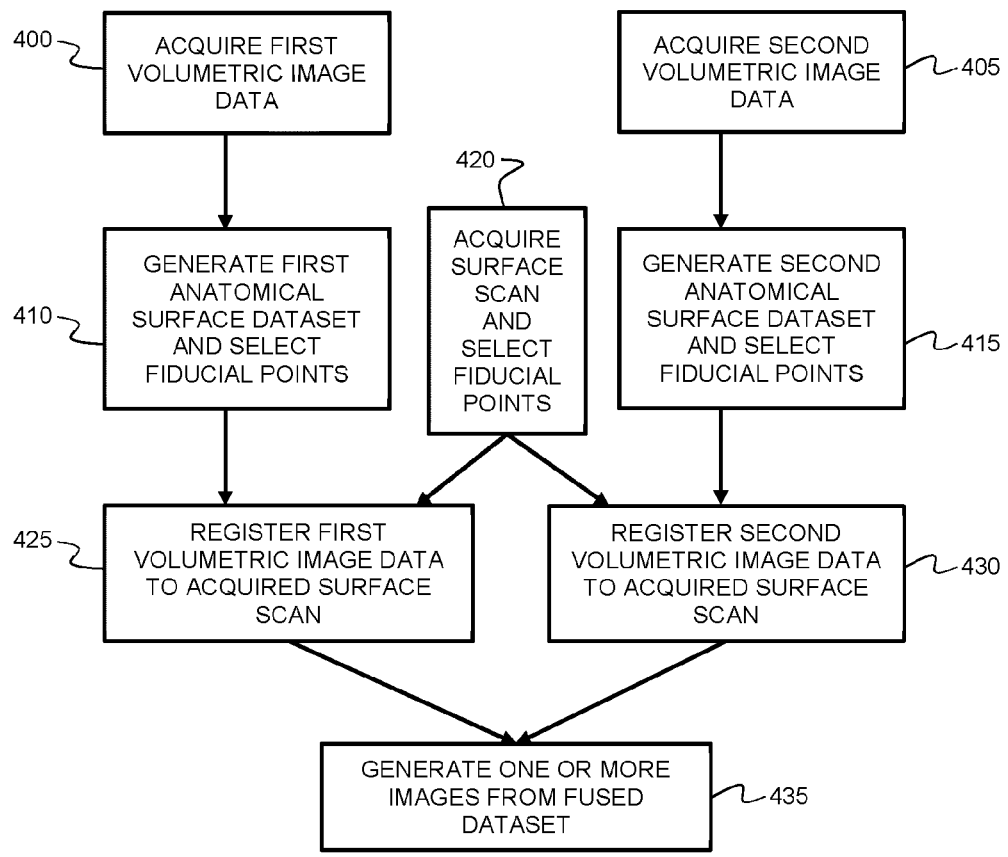
FIG. 3A is a flow chart illustrating an example method of performing image fusion between a first volumetric image dataset and a second volumetric image dataset using an intraoperatively detected surface for registration.

FIG. 3A illustrates one non-limiting example method of performing image fusion via an intraoperatively acquired surface dataset. In steps 400 and 405, first and second volumetric image datasets are acquired. The first and second volumetric image datasets may be obtained using, for example, imaging modalities such as, but not limited to, computed tomography (CT), magnetic resonance imaging (MRI) and ultrasound. Other examples of suitable imaging modalities for providing the volumetric image data include, but are not limited to, optical coherence tomography (OCT) and PET-CT. In some example embodiments, at least two of the volumetric image datasets may be obtained using different imaging modalities. In other example embodiments, at least two of the volumetric image datasets may be obtained using a common imaging modality.

In some example embodiments, one or more of the volumetric image datasets may be obtained pre-operatively, for example, using intraoperative CT or intraoperative MRI. In some example embodiments, one or more of the volumetric image datasets may be obtained intraoperatively, for example, using intraoperative CT or intraoperative MRI. It is noted that although FIG. 3A illustrates an image fusion method using two volumetric image datasets, the present example method is not limited to the fusion of two volumetric image datasets, and the method may be readily adapted to include the fusion of one or more additional volumetric image datasets.

As shown at steps 410 and 415, in order to perform registration of the first volumetric image data to the intraoperative surface data, first anatomical surface data is generated from the first volumetric image data, such that the anatomical surface data represents (e.g. characterizes) a surface region that overlaps, at least in part, with a first surface region of the subject that is expected or planned to be intraoperatively exposed during a surgical procedure. Similarly, second anatomical surface data is generated from the second volumetric image data, such that the second anatomical surface data represents (e.g. characterizes) a second surface region that overlaps, at least in part, with a surface region of the subject that is expected or planned to be intraoperatively exposed during a surgical procedure. The first and second regions may be equal or may overlap at least in part or not at all. For example, the first anatomical surface dataset may characterize a first skin region, and the second anatomical surface dataset may characterize a second skin region, where the first and second skin regions may overlap fully, in part, or not at all. The anatomical surface may be an external skin surface that is expected to be exposed and available for surface scanning during at least a portion of the surgical procedure. A skin surface is usually readily generated from both CT and MRI volumetric image data, providing a means to register both volumetric image datasets to the intraoperative surface.

In another example, the first anatomical surface dataset may characterize a first bone region, and the second anatomical surface dataset may characterize a second bone region, where the first and second bone regions overlap full, in part, or not at all. It is noted that although the identification of bone surface is readily achievable from a CT volumetric image dataset, a bone surface may not be easily extracted based on an MRI volumetric image dataset. Nonetheless, bone imaging MRI protocols are an active area of research by many large MRI manufacturers, and therefore it may be possible in the near future to process MRI data to extract surface data that is associated with a bone surface.

The anatomical surface data may be generated from a given volumetric image dataset according to a wide variety of methods. One example method involves the selection of a bone or skin threshold and generating an isosurface using the marching cubes algorithm from the volumetric image data. Another example method employs the construction of an isocontour from each 2D slice of a volumetric image data based on a bone threshold, and stitching the slices together into a 3D surface.

In order to permit an initial registration with the intraoperative surface data, at least three fiducial points may be provided by a user or operator, based on displayed images of the first and second anatomical surface datasets (also as shown in steps 410 and 415). In some example embodiments, one or more of the fiducial points identified in the first anatomical surface dataset may correspond to respective fiducial point(s) identified in the second anatomical surface dataset. In one example implementation, the fiducial points provided in the first anatomical surface dataset image may be defined to correspond to the fiducial points provided in the second anatomical surface dataset image (i.e. corresponding fiducial points in the first and second anatomical surface dataset images mark a common anatomical location). In other example implementations, the fiducial points provided in the first anatomical surface dataset image need not correspond to the fiducial points provided in the second anatomical surface dataset image, since the anatomical surfaces corresponding to the first and second anatomical surface regions may be different in the present example embodiment.

Having obtained the volumetric image datasets, and the associated fiducial points, intraoperative surface detection is then employed to detect and measure intraoperative surface data, as shown at step 420. The intraoperative surface data may be obtained as a single intraoperative image dataset or as multiple intraoperative image datasets with each intraoperative image dataset spanning different (an optionally overlapping) regions. The intraoperative surface detection step is performed such that at least a portion of the intraoperative surface data overlaps with each of the surface regions associated with the first volumetric image dataset and the second volumetric image dataset.

In order to facilitate an initial registration between the (first and second) anatomical surface data and the intraoperative surface data, user input may be provided identifying fiducial points in the intraoperative frame of reference that correspond to the respective fiducial points identified in the first and second anatomical surface data (also shown at step 420). In one example implementation, a user may employ a tracked probe (e.g. a probe having fiducial markers attached thereto that are tracked with a tracking system) to select the intraoperative fiducial points via contact with the subject at the anatomical locations corresponding to the fiducial points identified in the first and second anatomical surface data. In a second example implementation, a user may employ one or more input devices and the user interface to select fiducials on the first and second anatomical data and the intraoperative surface data. In a third example implementation, a user may utilize a combination of the two example methods described above, e.g. selecting a subset of fiducials employing tracked probed and selecting the remaining fiducials employing I/O devices and user interface.

As shown in steps 425 and 430 of FIG. 3A, registration is then performed between the first anatomical surface data and intraoperative surface data, and registration is also performed between the second anatomical surface data and the intraoperative surface data. Each registration may be performed first as an initial registration based the correspondence between the fiducial points identified in the anatomical surface data and the fiducials defined in the intraoperative surface data. Surface-to-surface registrations may then be performed between the first anatomical surface data and the intraoperative surface data, and between the second anatomical surface data and the intraoperative surface data.

The resulting registration transforms may then be employed to fuse the first volumetric image data and the second volumetric image data, and/or the first anatomical surface data and the second anatomical surface data, such that the respective first and second datasets are represented in a common frame of reference, using a common coordinate system.

In one example implementation, the common coordinate system may be that of the surface detection system. During navigated procedures, it may be more appropriate to work in a common coordinate system of both the surface detection system and the tracking system. One such common coordinate system is that of the reference frame, which is attached to the patient. The reference frame accounts for apparent changes to the patient position relative to the tracking system and/or surface detection, for example, due to the bed being moved or reorientation of the tracking system and/or surface detection system during the procedure. Since the reference frame remains in a fixed position relative to the patient, recording position/orientation information from tracked instruments or the surface detection system relative to the reference frame position/orientation (for example, as described in International PCT Patent Application No. PCT/CA2015/050939, titled "TRACKING MARKER SUPPORT STRUCTURE AND SURFACE REGISTRATION METHODS EMPLOYING THE SAME FOR PERFORMING NAVIGATED SURGICAL PROCEDURES", which is hereby incorporated by reference in its entirety) is sufficient to compensate for these apparent motions.

In another example embodiment, the resulting registration transforms may be employed to generate an initial alignment between the first volumetric image dataset and the second volumetric image dataset, and volumetric-to-volumetric registration may be subsequently performed.

Figure 3B:
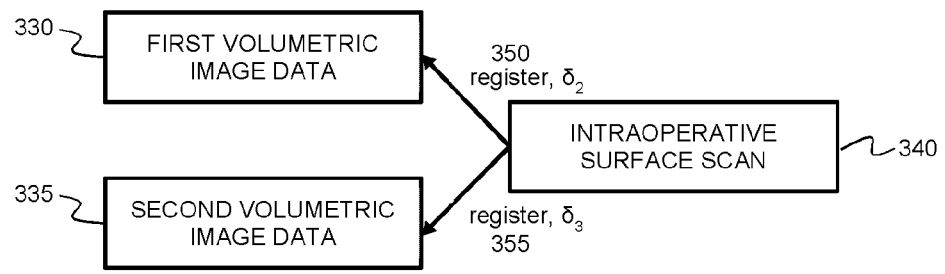
FIG. 3B illustrates the errors introduced when image fusion is performed according to the surface detection and registration method shown in FIG. 3A.

Referring now to FIG. 3B, the error in intraoperative surface detection based image fusion is shown to be smaller than the error associated with the conventional volumetric-to-volumetric image fusion method that was described with reference to FIGS. 1A and 1B. Unlike the direct fusion method, in which the error associated with the registration from the CT frame of reference to the intraoperative frame of reference is $\delta_1$ (see FIG. 1B), the error in registration 350 between the first volumetric image dataset (e.g. the CT dataset as per the example in FIG. 1B) and the intraoperative surface data is $\delta_2$, where $\delta_2 < \delta_1$, since registration step 350 involves a true surface-to-surface registration step, as opposed to a registration based on sparse fiducials, as in registration step 310 of FIG. 1B. Similarly, the error in registration 355 between the second volumetric image dataset (e.g. the MRI dataset as per the example in FIG. 1B) and the intraoperative surface data is $\delta_3$, where $\delta_3 < \delta_1 < \sqrt{\varepsilon_1^2 + \delta_1^2}$, since the registration step 355 involves a true surface-to-surface registration step, as opposed to a two-step registration based on both physical fiducial markers and the volumetric-to-volumetric registration method involving steps 300 and 310 of FIG. 1A.

It is also noted that unlike the conventional workflow shown in FIG. 1A, the surface-detection-based example method illustrated in FIG. 3A does not require artificial fiducials (physical fiducial markers attached to the subject) to be present when performing volumetric imaging to obtain the volumetric image datasets. The illustrated method therefore is capable of achieving the image fusion of volumetric image datasets, and the intraoperative generation of images based on the fused volumetric image datasets, without requiring direct volumetric-to-volumetric registration and fusion of the volumetric image datasets. The surface dataset therefore acts as an intermediate surface image-based reference, to which the volumetric image datasets may be registered. The independent registration of the volumetric-based isosurfaces to the intraoperative surface data provides a rapid and efficient image fusion method that is less sensitive to the propagation of error associated with fusion into the navigation phase.

Although the method described above is described as involving the registration of the anatomical surface data (first and second) with the intraoperative surface data, it will be understood that any one or more of the first anatomical surface data, the second anatomical surface data, and the intraoperative surface data may be segmented prior to performing the surface registration step. For example, a given surface may be initially segmented using at least one volumetric fiducial point associated with the surface to initialize a region growing surface segmentation method.

It is further noted that although the preceding example embodiment described the generation of anatomical surface datasets (isosurfaces) from the volumetric image datasets prior to having performed intraoperative surface detection, the anatomical surface datasets may alternatively be generated after having performed intraoperative surface detection, but prior to registration.

Figure 4:
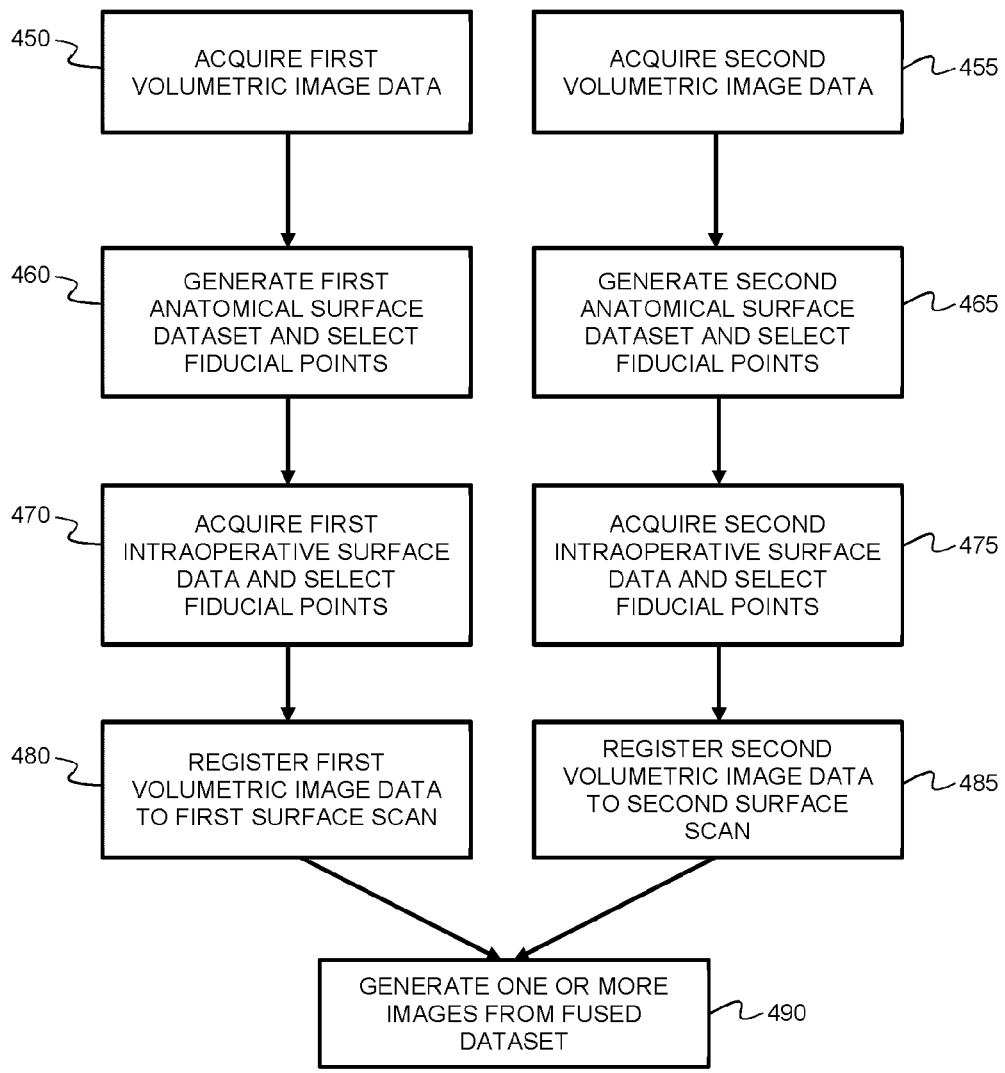
FIG. 4 is a flow chart illustrating an alternative example method of performing image fusion between a first volumetric image dataset and a second volumetric image dataset using intraoperatively detected surfaces for registration.

In the example method shown in FIG. 3A, the first and second anatomical surfaces generated from the first and second volumetric image datasets are separately registered to a common surface, based on intraoperative surface detection. FIG. 4 illustrates an alternative example embodiment in which the first and second volumetric image datasets are separately registered to different anatomical surfaces in order to achieve image fusion. As shown at steps 450 and 455, the first and second volumetric image datasets are obtained, as in steps 400 and 405 of FIG. 3A. However, in steps 460 and 465, the first and second volumetric image datasets are processed to extract respective anatomical surface datasets, such that the first anatomical surface dataset characterizes a first anatomical surface that is expected or planned to be intraoperatively exposed, and the second anatomical surface dataset characterizes a second anatomical surface that is also expected or planned to be intraoperatively exposed.

In the present example method, the first and second anatomical surfaces need not spatially overlap, and need not correspond to the same tissue type. For example, in one example implementation, the first and second anatomical surfaces may pertain to different skin regions, or different bone regions. In another example implementation, the first anatomical region may pertain to a skin region, and the second anatomical region may pertain to a bone region. Non-limiting examples of different combinations of tissue types for the first and second anatomical datasets include employing skin and bone (e.g. using MRI for skin and CT for bone), bone and brain (e.g. using CT for bone and MRI for brain), and skin and brain (e.g. using CT for skin and MRI for brain).

The first and second volumetric image datasets may be obtained at different times. For example, the first volumetric image dataset may be obtained pre-operatively, and the second volumetric image dataset may be obtained intraoperatively.

The first and second intraoperative surface datasets may also be obtained at different times. For example, the first intraoperative surface dataset (and associated fiducial points) may be obtained at a first point in time during a surgical procedure, and the second intraoperative surface dataset (and associated fiducial points) may be obtained at a different point in time during the surgical procedure.

In order to permit an initial registration with the intraoperative surface data, at least three fiducial points may be provided by a user or operator, based on displayed images of the first and second anatomical surface datasets (also as shown in steps 460 and 465). The fiducial points provided in the first anatomical surface dataset image need not correspond to the fiducial points provided in the second anatomical surface dataset image, since the anatomical surfaces corresponding to the first and second anatomical surface regions may be different in the present example embodiment.

Having obtained the volumetric image datasets, and the associated fiducial points, intraoperative surface detection is then employed to detect and measure intraoperative surface data, as shown at steps 470 and 475.

In one example embodiment, the intraoperative surface data may be obtained as separate scans, such that first intraoperative surface data is obtained that corresponds to the first anatomical surface dataset, and second intraoperative surface data is obtained that corresponds to the second anatomical surface dataset. For example, if the first anatomical surface dataset characterizes a skin surface, and the second anatomical surface dataset characterizes a bone surface, then the first intraoperative surface dataset is obtained by performing intraoperative surface detection of the respective skin region, and the second intraoperative surface dataset is obtained by performing intraoperative surface detection of the bone region.

In order to facilitate an initial registration between the (first and second) anatomical surface data with the respective first and second intraoperative surface datasets, user input may be provided identifying fiducial points in the intraoperative frame of reference that correspond to the respective fiducials identified in the first and second anatomical surface data (also shown at steps 470 and 475), such that first intraoperative fiducial points are identified that correspond to the fiducial points identified for the first anatomical surface dataset, and second intraoperative fiducial points are identified that correspond to the fiducial points identified for the second anatomical surface. In one example implementation, a user may employ a tracked probe (e.g. a probe having fiducial markers attached thereto that are tracked with a tracking system) to select the intraoperative fiducial points via contact with the subject at the anatomical locations corresponding to the fiducial points identified in the first and second anatomical surface data. In a second example implementation, a user may employ one or more input devices and the user interface to select fiducials on the first and second anatomical data and the intraoperative surface data. In a third example implementation, a user may utilize a combination of the two example methods described above (e.g. selecting a subset of fiducials employing tracked probed and selecting the remaining fiducials employing I/O devices and user interface.

As shown in steps 480 and 485 of FIG. 4, registration is then performed between the first anatomical surface data and first intraoperative surface data, and registration is also performed between the second anatomical surface data and the second intraoperative surface data. Each registration may be performed first as an initial registration based the correspondence between the fiducial points identified in the anatomical surface data and the fiducials defined in the intraoperative surface data. Surface-to-surface registrations may then be performed between the first anatomical surface data and the first intraoperative surface data, and between the second anatomical surface data and the second intraoperative surface data.

The resulting registration transforms may then be employed in step 490 to fuse the first volumetric image data and the second volumetric image data, and/or the first anatomical surface data and the second anatomical surface data, such that the respective first and second datasets are represented in a common frame of reference, using a common coordinate system. During navigated procedures, the common coordinate system may be, for example, that of the reference frame, which is attached to the patient. The reference frame accounts for apparent changes to the patient position relative to the tracking system and/or surface detection system, for example, due to the tracking system and/or surface detection system being reoriented between when the first and second intraoperative surface data being acquired.

In an alternative example embodiment, the intraoperative surface data may be obtained as a single scan that includes surface data corresponding to both the first anatomical surface dataset and the second anatomical surface dataset. For example, if the first anatomical surface dataset characterizes a skin surface, and the second anatomical surface dataset characterizes a bone surface, then an intraoperative surface dataset may be obtained by performing intraoperative surface detection over a surface region that includes both the skin region and the bone region. As in the preceding example embodiment, user input may be provided identifying fiducial points in the intraoperative frame of reference that correspond to the respective fiducial points identified in the first and second anatomical surface datasets, such that first intraoperative fiducial points are identified that correspond to the fiducial points identified for the first anatomical surface dataset, and second intraoperative fiducial points are identified that correspond to the fiducial points identified for the second anatomical surface. In some cases, in which there is spatial overlap between the first and second anatomical surface datasets, one or more of the fiducial points identified in the first anatomical surface dataset may correspond to respective fiducial point(s) identified in the second anatomical surface dataset. However, in general, the fiducial points provided in the first anatomical surface dataset image need not correspond to the fiducial points provided in the second anatomical surface dataset image, since the anatomical surfaces corresponding to the first and second anatomical surface regions may be different in the present example embodiment.

Although many of the preceding example embodiments involve the identification of fiducial points via user or operator input, it will also be understood that in other example implementations, some or all of the fiducial points may be identified automatically by processing surface data.

In some example embodiments, one or more of the fiducial points may be generated automatically using image processing methods to detect anatomical features and/or landmarks. In one example implementation, intraoperative fiducial points are generated using facial recognition to locate the position of the facial landmarks such as the eyes and nose the intraoperative surface image data. Image processing methods for the automated identification of anatomical features and/or landmarks. For example, the following algorithms may be employed for the identification of facial features and/or landmarks: Google's face detection API (https://www.sitepoint.com/face-detection-in-android-with-google-play-services/); face and eye detection using Haar Feature-based Cascade Classifiers (http://docs.opencv.org/trunk/d7/d8b/tutorial_py_face_detection.html); and the highly cited facial recognition system pioneered by Viola and Jones (viola01rapid.pdf) for recognizing the face, and subsequently different parts of the recognized faced, such as the eyes and the nose.

The two-dimensional image points corresponding to the detected anatomical features can then be re-projected into three-dimensional space using well-known camera calibration routines based on extrinsic and intrinsic parameters (e.g. focal, principal point, skew, distortion coefficients), for example, as described by Bradski et al. [G. Bradski and A. Kaehler, "Learning OpenCV", 2008].

Similarly, one or more of the fiducial points associated with the anatomical surface datasets can be automatically generated from the pre-operative volumetric image data. For example, the pre-operative volumetric image data can be processed using facial recognition methods on a two-dimensional image of the rendered volume. The detected two-dimensional image points can then be re-projected into three-dimensions using the render window camera parameters, as described above.

In some example implementations, one or both the anatomical surface data and the intraoperative surface data may be processed for the direct three-dimensional generation of fiducial points. This may be achieved, for example, using a model-based algorithm, in which a mathematical model of the patient anatomy is fitted or deformed to the surface data. In one example, a mathematical model of the cranial anatomy may include labels corresponding to the eye and/or nose (e.g. Collins et al-1995-Human Brain Mapping.pdf). In one example implementation, if three or more of the same features are detected in both the anatomical surface data and the intraoperative surface data, then the detected features can be employed as fiducial points when performing an initial landmark-based registration prior to surface-to-surface registration.

Figures 5A, 5B, 5C:
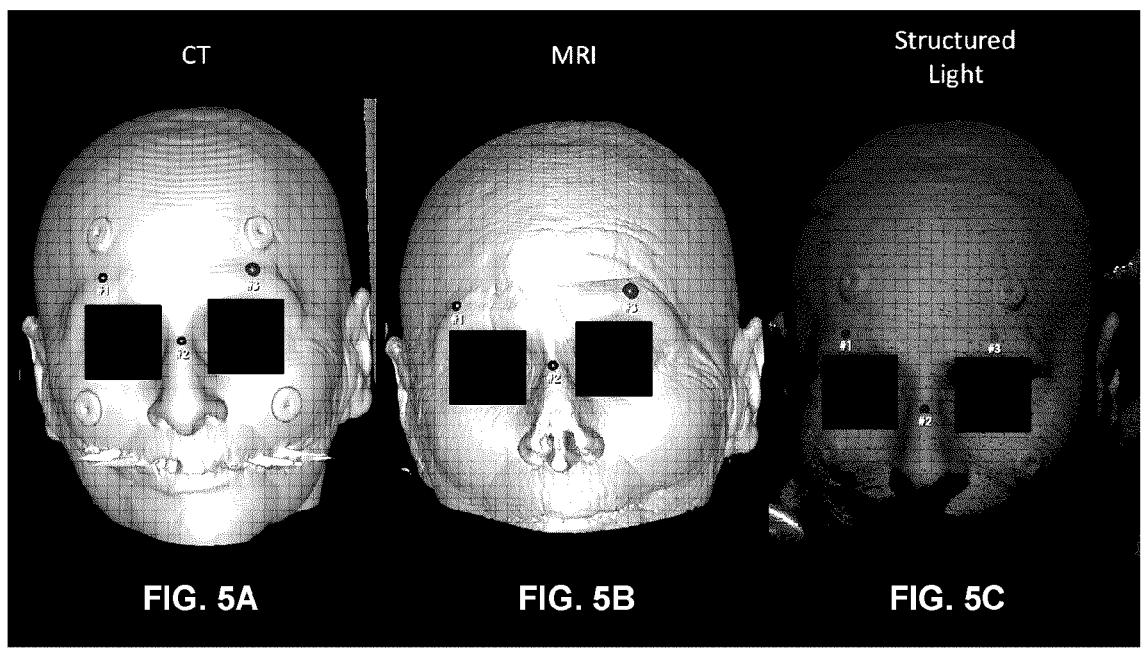
FIGS. 5A-C display images showing (A) the anatomical surface data pertaining to the skin surface as obtained from CT volumetric image data, (B) the anatomical surface data pertaining to the skin surface as obtained from MRI volumetric image data, and (C) the intraoperative surface data pertaining to the skin surface as obtained from intraoperative structured light surface detection. The region around the eyes has been removed in order to remove identifying features from the images.

Referring now to FIGS. 5A-C, an example embodiment is illustrated showing how a user interface may be used to display images showing (A) and first anatomical surface data pertaining to the skin surface as obtained from CT volumetric image data, (B) an second anatomical surface data pertaining to the skin surface as obtained from MRI volumetric image data, and (C) the intraoperative surface data pertaining to the skin surface as obtained from intraoperative structured light surface detection. It is noted that the region around the eyes has been removed in order to remove identifying features from the images. As described above, at least three fiducials are shown on each of the surface datasets which are used to facilitate the registration process.

Figure 6A:
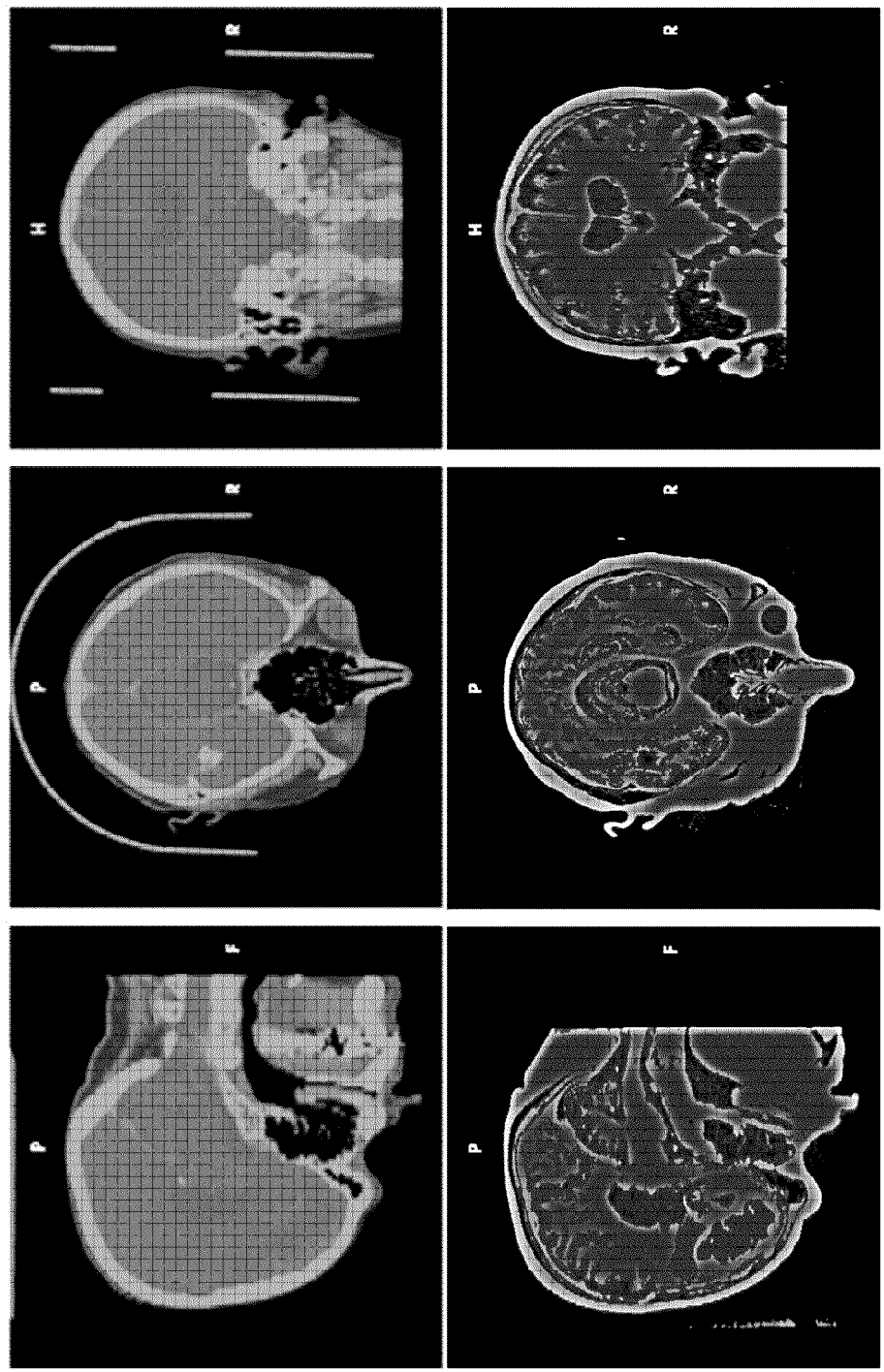
FIG. 6A is an example of a user interface providing windows displaying images showing sliced volumetric image data from a first fused volumetric image dataset, and other images showing sliced volumetric image data from a second fused volumetric image dataset, where the two volumetric image datasets are fused according to an example method of the present disclosure.
Figure 6B:
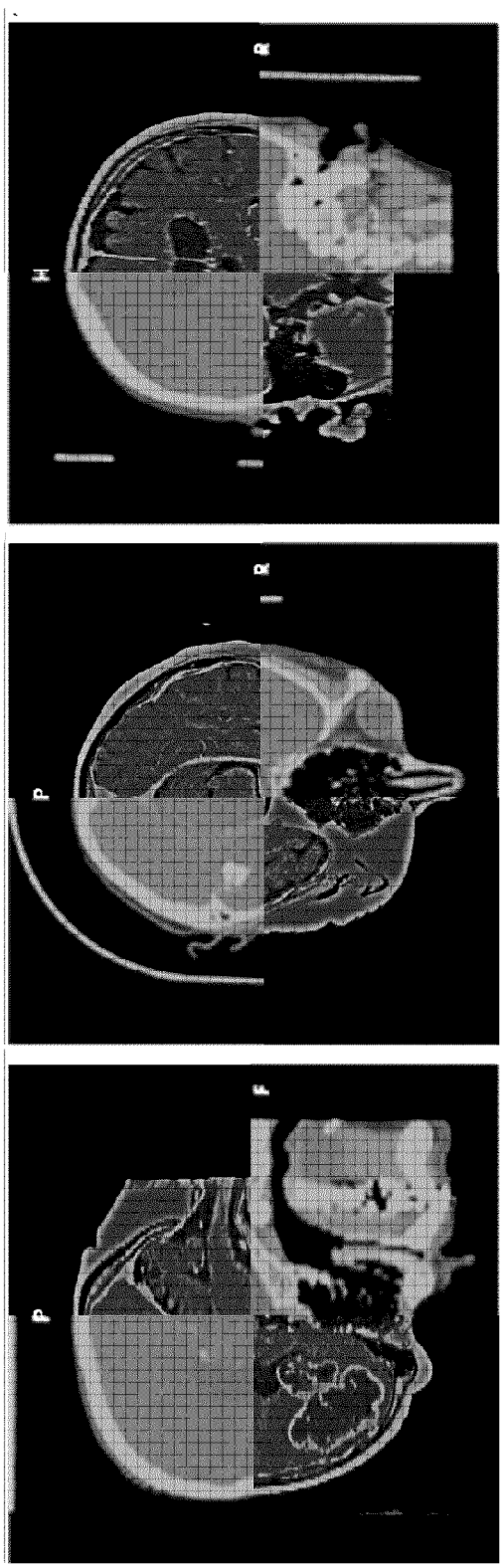
FIG. 6B is an example of a user interface providing windows displaying images in which some image regions show sliced volumetric image data from a first fused volumetric image dataset, and other image regions show sliced volumetric image data from a second fused volumetric image dataset, where the two volumetric image datasets are fused according to an example method of the present disclosure.

The fused dataset can be processed according to a wide variety of methods to support different visualizations. For example, the fused data can be resliced and visualized with respect to tracked tools. In the example embodiment shown in FIG. 6A, axial, sagittal and coronal views for both the fused MRI and CT datasets may be shown independently. Alternatively, the user may opt to view a subset of the available views. In a second example embodiment shown in FIG. 6B, a fused image may be generated for visualization having multiple image regions, where one or more first regions of the fused image include image data associated with the first volumetric image dataset, and one or more second regions of the fused image include image data associated with the second volumetric image dataset. The one or more first regions and the one or more second regions vary with time in the fused image, for example, by switching a given region from displaying include image data associated with one volumetric image dataset to displaying include image data associated with another volumetric image dataset, or, for example, by rotating the regions. The different image regions may be user selectable. Such example implementations may be useful for verifying registration, as further described below.

Figure 6C:
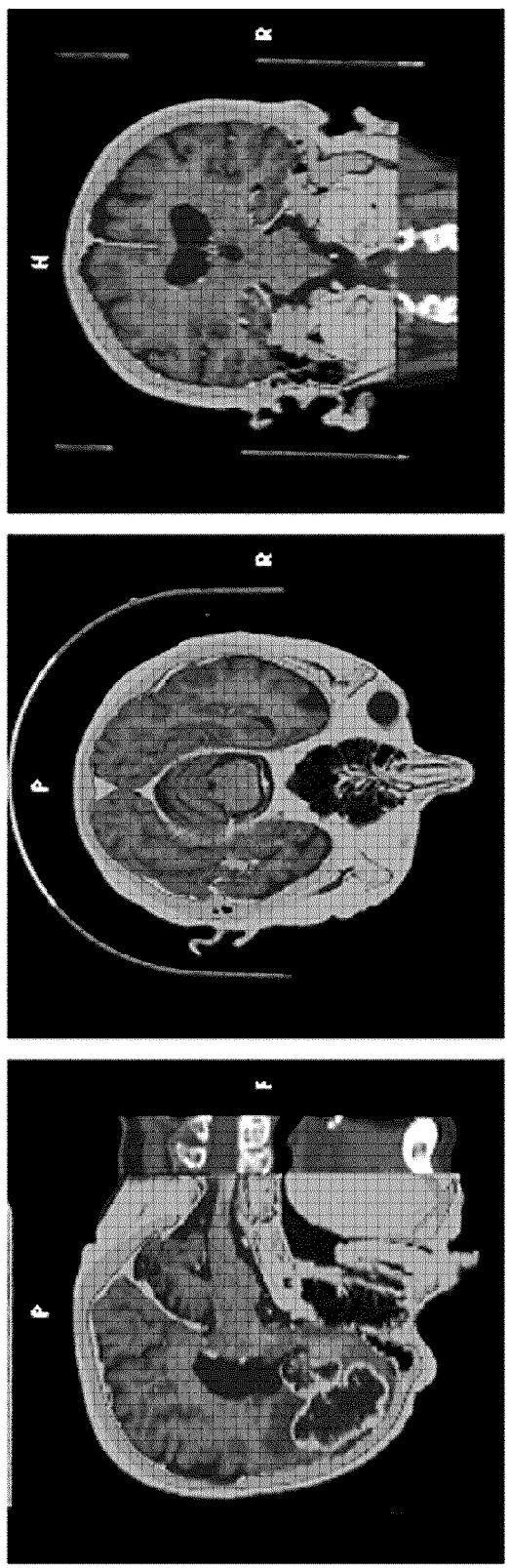
FIG. 6C is an example of a user interface displaying images in which image data from a first fused volumetric image dataset is overlaid, in a common image region, with image data from a second fused volumetric image dataset, where the two volumetric image datasets are fused according to an example method of the present disclosure.

In a third example embodiment shown in FIG. 6C, a fused image may be generated with the first and second volumetric data represented with different colors and overlaid over one another with transparency enabling the user to visualize the datasets concurrently.

In one example embodiment, the fusion of two or more volumetric image datasets may be verified. For example, verification can be performed sequentially, as a two stage verification process, in which the registration of each volumetric imaging modality is confirmed by an operator. According to the present example method, the user/operator would first be presented with a display showing image data based on one of the registered imaging modalities, displayed with the overlay of a tracked tool. The operator may then contact various anatomical landmarks with the tracked tool on the subject and visually confirm that the displayed locations of the tracked tool, relative to the displayed image data, corresponded to the correct anatomical locations. Once the registration of the first imaging modality is confirmed, verifying the accuracy of the first registration, the registration of the second imaging modality would be verified according to a similar method.

In an alternative example implementation, the registration and image fusion could be verified based on the display, relative to a tracked tool, of fused image data from both volumetric imaging datasets, allowing the operator to visually assess the correct orientation of a tracked tool relative to anatomical features seen in both imaging modalities.

In one example implementation, the registration could be assessed by displaying, relative to a tracked tool, image data from both volumetric image datasets, where the display of the image data from one volumetric image dataset is temporally and/or spatially interleaved (multiplexed) with the display of the image data from another volumetric image dataset.

The preceding example embodiments, although illustrated through examples involving cranial procedures (e.g. neurosurgery), can be applied to a broad range of medical procedures involving the collection and fusion of multiple volumetric image datasets. The methods and systems described here may be applied to procedures involving a wide range of anatomical regions at various locations of the body.

For example, in one example embodiment, the preceding methods may be applied to surgical procedures involving total or partial knee replacement (robotic or manual). The articular cartilage of the knee can be segmented from either an MRI scan or CT scan, and the articular cartilage is therefore a suitable surface for registration via surface detection. Accordingly, in one example implementation involve knee surgery, preoperative CT and MRI volumetric image data is processed to obtain anatomical surface data characterizing the articular cartilage. The articular cartilage of the knee is surgically exposed and intraoperative surface data characterizing the surface of the articular cartilage is detected via a surface detection system. The CT and MRI volumetric image datasets are then separately registered to the intraoperative surface data, thus fusing the two volumetric image datasets, allowing visualization of CT and MRI image data in navigation images. A surgeon may then use a navigated drill (manual or robotic) to start removing the cartilage and bone in order to place the implant.

In another example implementation, embodiments of the present disclosure may be adapted for use in spine surgery, for example, to enable a surgeon to better delineate soft tissue. For example, the preceding example embodiments may be employed in a minimally invasive scenario in spine surgery where screws are placed percutaneously through the skin. In such a case, both the CT and MRI scan could be registered to a surface scan (e.g. a structured light scan) of the skin and/or other artificial fiducials. Other non-limiting examples of surgical applications to which the present embodiments may be adapted include surgical procedures involving the hip and shoulder.

The example embodiments disclosed herein may also be adapted for use in surgical procedures involving soft tissue targets, such as, but not limited to, breast, prostate, and brain surface targets, which may benefit from the use of deformable registration methods. Non-limiting examples of deformable registration methods include kernel splines methods (such as thin plates, thin plates R2 log R, elastic body, elastic body reciprocal, and volume) and demon registration methods and its variants. In the case of deformable registration, the output transformation may be, for example, a vector field or a mapping function which transforms points from one coordinate system to the other.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing intraoperative image registration, the method comprising:
    obtaining a first volumetric image dataset pertaining to a subject;
    obtaining a second volumetric image dataset pertaining to the subject;
    processing the first volumetric image dataset to generate a first anatomical surface dataset from the first volumetric image dataset, the first anatomical surface dataset characterizing a first anatomical surface region;
    processing the second volumetric image dataset to generate a second anatomical surface dataset from the second volumetric image dataset, the second anatomical surface dataset characterizing a second anatomical surface region;
    receiving input identifying at least three first fiducial points associated with the first surface dataset;
    receiving input identifying at least three second fiducial points associated with the second surface dataset;
    intraoperatively detecting, with a surface detection subsystem, intraoperative surface data characterizing an intraoperatively exposed surface region, wherein the intraoperatively exposed surface region overlaps with at least a portion of the first anatomical surface region and at least a portion of the second anatomical surface region;
    obtaining input identifying at least three intraoperative fiducial points in an intraoperative frame of reference associated with the intraoperative surface data, such that each fiducial point from the first fiducial points and the second fiducial points has a corresponding intraoperative fiducial point;
    employing the first fiducial points and the corresponding intraoperative fiducial points to perform registration between the first anatomical surface dataset and the intraoperative surface data, thereby obtaining a first registration transform;
    employing the second fiducial points and the corresponding intraoperative fiducial points to perform registration between the second anatomical surface dataset and the intraoperative surface data, thereby obtaining a second registration transform; and
    employing the first registration transform and the second registration transform to transform the first volumetric image dataset and the second volumetric image dataset into a common frame of reference, thereby obtaining a fused dataset; and
    generating one or more images based on the fused dataset.

2. The method according to claim 1 wherein at least one of the one or more images is a fused image comprising at least a portion of the first volumetric image dataset and at least a portion of the second volumetric image dataset.

3. The method according to claim 2 wherein one or more first regions of the fused image comprises image data associated with the first volumetric image dataset, and one or more second regions of the fused image comprises image data associated with the second volumetric image dataset.

4. The method according to claim 3 wherein the one or more first regions and the one or more second regions vary with time in the fused image.

5. The method according to claim 3 wherein the one or more first regions and the one or more second regions are user-selectable.

6. The method according to claim 1 wherein one or more of the first volumetric image dataset and the second volumetric image dataset were acquired in the absence of the application of fiducial markers onto or within the subject.

7. The method according to claim 1 wherein the first volumetric image dataset and the second volumetric image dataset were obtained using different imaging modalities.

8. The method according to claim 7 wherein the first volumetric image dataset was obtained using computed tomography (CT) and the second volumetric image dataset was obtained using magnetic resonance imaging (MRI).

9. The method according to claim 1 wherein the first volumetric image dataset and the second volumetric image dataset were obtained using a common imaging modality, and wherein the first volumetric image dataset and the second volumetric image dataset were obtained at different points in time.

10. The method according to claim 9 wherein the first volumetric image dataset is obtained pre-operatively, and the second volumetric image dataset is obtained intraoperatively.

11. The method according to claim 1 wherein said surface detection subsystem is a structured light detection system.

12. The method according to claim 1 further comprising displaying, in at least one of the one or more images, navigation information associated with one or more tracked instruments.

13. The method according to claim 1 further comprising performing employing the alignment of the first volumetric image dataset and the second volumetric image dataset in the fused dataset to perform a subsequent image registration between the first volumetric image dataset and the second volumetric image dataset.

14. A system for performing intraoperative image registration, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
obtaining a first volumetric image dataset pertaining to a subject;
obtaining a second volumetric image dataset pertaining to the subject;
processing the first volumetric image dataset to generate a first anatomical surface dataset from the first volumetric image dataset, the first anatomical surface dataset characterizing a first anatomical surface region;
processing the second volumetric image dataset to generate a second anatomical surface dataset from the second volumetric image dataset, the second anatomical surface dataset characterizing a second anatomical surface region;
receiving input identifying at least three first fiducial points associated with the first surface dataset;
receiving input identifying at least three second fiducial points associated with the second surface dataset;
controlling said surface detection subsystem to intraoperatively detect intraoperative surface data characterizing an intraoperatively exposed surface region, wherein the intraoperatively exposed surface region overlaps with at least a portion of the first anatomical surface region and at least a portion of the second anatomical surface region;
obtaining input identifying at least three intraoperative fiducial points in an intraoperative frame of reference associated with the intraoperative surface data, such that each fiducial point from the first fiducial points and the second fiducial points has a corresponding intraoperative fiducial point;
employing the first fiducial points and the corresponding intraoperative fiducial points to perform registration between the first anatomical surface dataset and the intraoperative surface data, thereby obtaining a first registration transform;
employing the second fiducial points and the corresponding intraoperative fiducial points to perform registration between the second anatomical surface dataset and the intraoperative surface data, thereby obtaining a second registration transform; and
employing the first registration transform and the second registration transform to transform the first volumetric image dataset and the second volumetric image dataset into a common frame of reference, thereby obtaining a fused dataset; and
generating one or more images based on the fused dataset.

15. A method of performing intraoperative image registration, the method comprising:
obtaining a first volumetric image dataset pertaining to a subject;
obtaining a second volumetric image dataset pertaining to the subject;
processing the first volumetric image dataset to generate a first anatomical surface dataset from the first volumetric image dataset, the first anatomical surface dataset characterizing a first anatomical surface region;
processing the second volumetric image dataset to generate a second anatomical surface dataset from the second volumetric image dataset, the second anatomical surface dataset characterizing a second anatomical surface region;
receiving input identifying at least three first fiducial points associated with the first surface dataset;
receiving input identifying at least three second fiducial points associated with the second surface dataset;
intraoperatively detecting, with a surface detection subsystem, first intraoperative surface data characterizing a first intraoperatively exposed surface region, wherein the first intraoperatively exposed surface region overlaps with at least a portion of the first anatomical surface region;
intraoperatively detecting, with the surface detection subsystem, second intraoperative surface data characterizing a second intraoperatively exposed surface region, wherein the second intraoperatively exposed surface region overlaps with at least a portion of the second anatomical surface region;
obtaining input identifying at least three primary intraoperative fiducial points in an intraoperative frame of reference, wherein each primary intraoperative fiducial point corresponds to a respective first fiducial point;
obtaining input identifying at least three secondary intraoperative fiducial points in the intraoperative frame of reference, wherein each secondary intraoperative fiducial point corresponds to a respective second fiducial point;
employing the first fiducial points and the corresponding primary intraoperative fiducial points to perform registration between the first anatomical surface dataset and the first intraoperative surface data, thereby obtaining a first registration transform;
employing the second fiducial points and the corresponding secondary intraoperative fiducial points to perform registration between the second anatomical surface dataset and the second intraoperative surface data, thereby obtaining a second registration transform; and
employing the first registration transform and the second registration transform to transform the first volumetric image dataset and the second volumetric image dataset into a common frame of reference, thereby obtaining a fused dataset; and generating one or more images based on the fused dataset.

16. The method according to claim 15 wherein at least one of the one or more images is a fused image.

17. The method according to claim 16 wherein one or more first regions of the fused image comprises image data associated with the first volumetric image dataset, and one or more second regions of the fused image comprises image data associated with the second volumetric image dataset.

18. The method according to claim 17 wherein the one or more first regions and the one or more second regions vary with time in the fused image.

19. The method according to claim 17 wherein the one or more first regions and the one or more second regions are user-selectable.

20. The method according to claim 15 wherein the first anatomical surface dataset is associated with a bone surface and the second anatomical surface dataset is associated with a skin surface.

21. The method according to claim 15 wherein the first anatomical surface region and the second anatomical surface region are associated with different tissue types.

22. The method according to claim 15 wherein the first intraoperative surface data and the second intraoperative surface data are acquired at different times during a surgical procedure.

23. The method according to claim 22 wherein the first volumetric image dataset is obtained preoperatively, and the second volumetric image dataset is obtained intraoperatively.

24. The method according to claim 15 wherein one or more of the first volumetric image dataset and the second volumetric image dataset were acquired in the absence of the application of fiducial markers onto or within the subject.

25. The method according to claim 15 wherein the first volumetric image dataset and the second volumetric image dataset were obtained using different imaging modalities.

26. The method according to claim 25 wherein the first volumetric image dataset was obtained using computed tomography (CT) and the second volumetric image dataset was obtained using magnetic resonance imaging (MRI).

27. The method according to claim 15 wherein said surface detection subsystem is a structured light detection system.

28. The method according to claim 15 further comprising displaying, in at least one of the one or more images, navigation information associated with one or more tracked instruments.

29. The method according to claim 15 further comprising performing employing the alignment of the first volumetric image dataset and the second volumetric image dataset in the fused dataset to perform a subsequent image registration between the first volumetric image dataset and the second volumetric image dataset.

30. A system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

receiving input identifying at least three first fiducial points associated with the first surface dataset;

receiving input identifying at least three second fiducial points associated with the second surface dataset;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

controlling said surface detection subsystem to intraoperatively detect intraoperative surface data characterizing a second intraoperatively exposed surface region, wherein the second intraoperatively exposed surface region overlaps with at least a portion of the second anatomical surface region;

obtaining input identifying at least three primary intraoperative fiducial points in an intraoperative frame of reference, wherein each primary intraoperative fiducial point corresponds to a respective first fiducial point;

obtaining input identifying at least three secondary intraoperative fiducial points in the intraoperative frame of reference, wherein each secondary intraoperative fiducial point corresponds to a respective second fiducial point;

employing the first fiducial points and the corresponding primary intraoperative fiducial points to perform registration between the first anatomical surface dataset and the first intraoperative surface data, thereby obtaining a first registration transform;

employing the second fiducial points and the corresponding secondary intraoperative fiducial points to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

31. A method of performing intraoperative image registration, the method comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, intraoperative surface data characterizing an intraoperatively exposed surface region, wherein the intraoperatively exposed surface region overlaps with at least a portion of the first anatomical surface region and at least a portion of the second anatomical surface region;

employing first fiducial points identified within the first anatomical surface dataset and corresponding intraoperative fiducial points identified in the intraoperative surface data to perform registration between the first anatomical surface dataset and the intraoperative surface data, thereby obtaining a first registration transform;

employing second fiducial points identified within the second anatomical surface dataset and corresponding intraoperative fiducial points identified in the intraoperative surface data to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

32. A system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

controlling said surface detection subsystem to intraoperatively detect intraoperative surface data characterizing an intraoperatively exposed surface region, wherein the intraoperatively exposed surface region overlaps with at least a portion of the first anatomical surface region and at least a portion of the second anatomical surface region;

employing first fiducial points identified within the first anatomical surface dataset and corresponding intraoperative fiducial points identified within the intraoperative surface data to perform registration between the first anatomical surface dataset and the intraoperative surface data, thereby obtaining a first registration transform;

employing second fiducial points identified within the second anatomical surface dataset and corresponding intraoperative fiducial points identified within the intraoperative surface dataset to perform registration between the second anatomical surface dataset and the intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

33. A method of performing intraoperative image registration, the method comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

intraoperatively detecting, with the surface detection subsystem, second intraoperative surface data characterizing a second intraoperatively exposed surface region, wherein the second intraoperatively exposed surface region overlaps with at least a portion of the second anatomical surface region;

employing first fiducial points identified within the first anatomical surface dataset and corresponding primary intraoperative fiducial points identified within the first intraoperative surface data to perform registration between the first anatomical surface dataset and the first intraoperative surface data, thereby obtaining a first registration transform;

employing second fiducial points identified within the second anatomical surface dataset and corresponding secondary intraoperative fiducial points identified within the second intraoperative surface data to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

34. A system for performing intraoperative image registration, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

obtaining a first volumetric image dataset pertaining to a subject;

obtaining a second volumetric image dataset pertaining to the subject;

processing the first volumetric image dataset to generate a first anatomical surface dataset from the first volumetric image dataset, the first anatomical surface dataset characterizing a first anatomical surface region;

processing the second volumetric image dataset to generate a second anatomical surface dataset from the second volumetric image dataset, the second anatomical surface dataset characterizing a second anatomical surface region;

intraoperatively detecting, with a surface detection subsystem, first intraoperative surface data characterizing a first intraoperatively exposed surface region, wherein the first intraoperatively exposed surface region overlaps with at least a portion of the first anatomical surface region;

controlling said surface detection subsystem to intraoperatively detect intraoperative surface data characterizing a second intraoperatively exposed surface region, wherein the second intraoperatively exposed surface region overlaps with at least a portion of the second anatomical surface region;

employing first fiducial points identified within the first anatomical surface dataset and corresponding primary intraoperative fiducial points identified within the first intraoperative surface dataset to perform registration between the first anatomical surface dataset and the first intraoperative surface data, thereby obtaining a first registration transform;

employing second fiducial points identified within the second anatomical surface dataset and corresponding secondary intraoperative fiducial points identified within the second anatomical surface dataset to perform registration between the second anatomical surface dataset and the second intraoperative surface data, thereby obtaining a second registration transform; and employing the first registration transform and the second registration transform to transform the first volumetric image dataset and the second volumetric image dataset into a common frame of reference, thereby obtaining a fused dataset; and generating one or more images based on the fused dataset.

* * * * *